(12) United States Patent
Leff et al.

(10) Patent No.: US 12,076,054 B2
(45) Date of Patent: *Sep. 3, 2024

(54) ORTHOPEDIC FIXATION DEVICES AND METHODS THEREOF

(71) Applicant: GLOBUS MEDICAL, INC., Audubon, PA (US)

(72) Inventors: David Leff, Philadelphia, PA (US); Matthew Bechtel, Philadelphia, PA (US); Patrick Murray, Collegeville, PA (US); David Peretz, Wynnewood, PA (US); Noah Hansell, King of Prussia, PA (US); Jeff Nichols, Medford, NJ (US); George Yacoub, Conshohocken, PA (US); Patrick Taggart, Philadelphia, PA (US)

(73) Assignee: Globus Medical, Inc, Audubon, PA (US)

( * ) Notice: Subject to any disclaimer, the term of this patent is extended or adjusted under 35 U.S.C. 154(b) by 396 days.

This patent is subject to a terminal disclaimer.

(21) Appl. No.: 17/504,874

(22) Filed: Oct. 19, 2021

(65) Prior Publication Data

US 2022/0257289 A1 Aug. 18, 2022

Related U.S. Application Data

(63) Continuation of application No. 17/176,435, filed on Feb. 16, 2021, now Pat. No. 11,191,573.

(51) Int. Cl.
*A61B 17/70* (2006.01)

(52) U.S. Cl.
CPC ...... *A61B 17/7037* (2013.01); *A61B 17/7032* (2013.01)

(58) Field of Classification Search
CPC ............ A61B 17/7032; A61B 17/7035; A61B 17/7037
See application file for complete search history.

(56) References Cited

U.S. PATENT DOCUMENTS

| | | | | |
|---|---|---|---|---|
| 11,191,573 B1* | 12/2021 | Leff | ............... | A61B 17/7037 |
| 2011/0152947 A1* | 6/2011 | Kirschman | ........ | A61B 17/8665 606/208 |
| 2012/0150239 A1* | 6/2012 | Garamszegi | ....... | A61B 17/8052 606/328 |
| 2014/0277157 A1* | 9/2014 | Chandanson | ...... | A61B 17/7032 606/278 |
| 2016/0361096 A1* | 12/2016 | van der Pol | ....... | A61B 17/7076 |

\* cited by examiner

*Primary Examiner* — Eduardo C Robert
*Assistant Examiner* — Michelle C Eckman

(57) ABSTRACT

Orthopedic fixation devices, assemblies, and methods for securing a spinal rod. The orthopedic fixation device may include a tulip head, a bone fastener, a rotatable saddle, and a threaded locking cap. The saddle may be insertable into the tulip head in an unlocked position with a rod seat offset relative to a rod slot of the tulip head. The saddle may be rotated into a locked position with the rod seat aligned with the rod slot such that a rod is positionable through the rod slot and into the rod seat. The threaded locking cap may secure the rod and bone fastener.

14 Claims, 15 Drawing Sheets

ORTHOPEDIC FIXATION DEVICES AND METHODS THEREOF

CROSS REFERENCE TO RELATED APPLICATIONS

The present application is a continuation application of U.S. patent application Ser. No. 17/176,435 filed on Feb. 16, 2021 which is incorporate in its entirety herein.

FIELD OF THE INVENTION

The present application relates generally to orthopedic fixation devices, and more particularly, bone fastener assemblies, for example, for spine surgery.

BACKGROUND OF THE INVENTION

Many types of spinal irregularities cause pain, limit range of motion, or injure the nervous system within the spinal column. These irregularities may result from, without limitations, trauma, tumor, disc degeneration, and disease. Often, these irregularities are treated by immobilizing a portion of the spine. This treatment typically involves affixing one or more bone fasteners, such as screws, hooks, or clamps, to one or more vertebrae and connecting the bone fastener(s) to an elongate spinal rod that stabilizes members of the spine.

The bone fixation device may include a tulip head for coupling the bone fastener to the elongate spinal rod. A locking cap may be used to secure the elongate spinal rod in the tulip head. There exists a need for improved functionality, strength, and/or ease of manufacturing of the bone fixation components.

SUMMARY OF THE INVENTION

To meet this and other needs, bone fastener devices, assemblies, implants, systems, and methods of treating spinal irregularities are provided. The implant or assembly may include a tulip head with a locking cap for securing the spinal rod therein. The implant may be configured for use with a variety of screws, such as polyaxial, uniplanar, monoaxial, reduction, modular, etc. The bone fastener may be implanted, for example, in open, semi-open, or percutaneous approaches to the posterior spine.

According to one embodiment, an orthopedic fixation assembly includes a tulip head, a bone fastener, a saddle, and a locking cap. The tulip head may include two arms defining a rod slot therebetween. The tulip head defines a bore extending therethrough and a groove disposed about the bore. The bone fastener includes a screw head receivable in the tulip head and a shaft configured for engaging bone. The saddle includes an upper surface defining a rod seat. The saddle is configured to secure the screw head of the bone fastener. The saddle is insertable into the tulip head in a first position with the rod seat offset relative to the rod slot. The saddle is rotatable into a second position with the rod seat aligned with the rod slot such that a rod is positionable through the rod slot and into the rod seat. The threaded locking cap is threadable between the two arms of the tulip head to secure the rod therein.

The assembly may include one or more of the following features. The saddle may be twisted or rotated, for example, 90° about a central longitudinal axis of the tulip head from the first position to the second position. An outer surface of the saddle and the groove may be elliptically shaped, thereby preventing the saddle from rotating out of alignment. One or more relief cuts in the tulip head may lead into the groove to allow rotation of the saddle into alignment in a single direction. The saddle may include a through bore and a pair of engagement recesses in the upper surface of the saddle on opposite sides of the through bore. The engagement recesses may be configured to interface with an assembly tool to facilitate rotation of the saddle. The saddle may include a pair of wings extending outwardly from opposite sides of the saddle. The wings may be receivable in the groove in the tulip head. When the locking cap is threaded downwardly onto the rod, the rod may be pushed against the seat of the saddle, thereby allowing the saddle to secure the bone fastener. The bore of the tulip head may define an internal taper such that the screw head is prevented from disengaging from the tulip head by the internal taper. Alternatively, the assembly may include a split ring or clip to secure the bone fastener. The assembly may further include a clamp for accepting the screw head. When the saddle is in the first position, the clamp is able to accept the screw head, and when the saddle is in the second position, the bone fastener is locked in position.

According to another embodiment, an orthopedic fixation device includes a tulip head, a locking cap, and a saddle. The tulip head may have two arms defining a rod slot therebetween. Each of the arms defines a threaded portion along an interior surface. The tulip head has a bore extending therethrough and a groove disposed about the bore. The tulip head may define a first indicator. The locking cap may have an outer body defining a thread. The locking cap is threadable between the two arms of the tulip head to secure a rod therein. The locking cap may define a second indicator to show the best alignment to start threading the locking cap into the tulip head. The saddle may have an upper surface defining a rod seat. The saddle is insertable into the tulip head in an unlocked position with the rod seat offset relative to the rod slot, and the saddle is rotatable into a locked position with the rod seat aligned with the rod slot such that a rod is positionable through the rod slot and into the rod seat.

The device may include one or more of the following features. The first indicator may include at least one laser mark on an upper surface of one of the arms. The second indicator may be a groove extending radially outward on a top surface of the locking cap. The device may include a third indicator including a cutout in a side of one of the arms. The locking cap may have a first thread at a bottom of the locking cap. The first thread may be broken by a radiused cut, thereby increasing the likelihood of the thread engaging with the threaded portion of the tulip head. Starts of the threads of the locking cap and tulip head may be timed when the first indicator and second indicators are aligned, thereby helping to avoid off angle insertion. The thread of the locking cap may include a top surface angled inward towards a minor diameter and a bottom surface angled outward away from the minor diameter.

According to yet another embodiment, a method of installing an orthopedic fixation device may include one or more of the following: (1) providing a tulip head having two arms defining a rod slot therebetween, the tulip head having a bore extending therethrough and a groove disposed about the bore; (2) inserting a saddle into the tulip head in an unlocked position, the saddle having an upper surface defining a rod seat, wherein the rod seat is inserted offset relative to the rod slot; and (3) rotating the saddle 90° into a locked position such that the rod seat is aligned with the rod slot and a rod is positionable through the rod slot and into the rod seat.

The method may also include one or more of the following: (4) inserting a screw head of a polyaxial bone fastener into the tulip head and saddle; (5) positioning a rod between the two arms and into the rod slot of the tulip head; and/or (6) threading a locking cap downwardly between the two arms of the tulip head, wherein the rod presses against the rod seat of the saddle, and the saddle presses against the screw head, thereby securing the rod and bone fastener.

Also provided are kits including implants of varying types and sizes, rods, various instruments and tools, and other components for performing the procedure.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein:

FIG. 22 shows a perspective view of the saddle according to one embodiment; and

DETAILED DESCRIPTION OF THE INVENTION

Embodiments of the disclosure are generally directed to orthopedic devices, assemblies, implants, systems, and methods for securing a spinal rod during spine surgery. Specifically, embodiments are directed tulip assemblies configured to secure a spinal rod to a bone fastener. Although described with reference to the spine, it will be appreciated that the devices and systems described herein may be applied to other orthopedic locations and applications, such as trauma.

Additional aspects, advantages and/or other features of example embodiments of the invention will become apparent in view of the following detailed description. It should be apparent to those skilled in the art that the described embodiments provided herein are merely exemplary and illustrative and not limiting. Numerous embodiments or modifications thereof are contemplated as falling within the scope of this disclosure and equivalents thereto.

Figure 1:
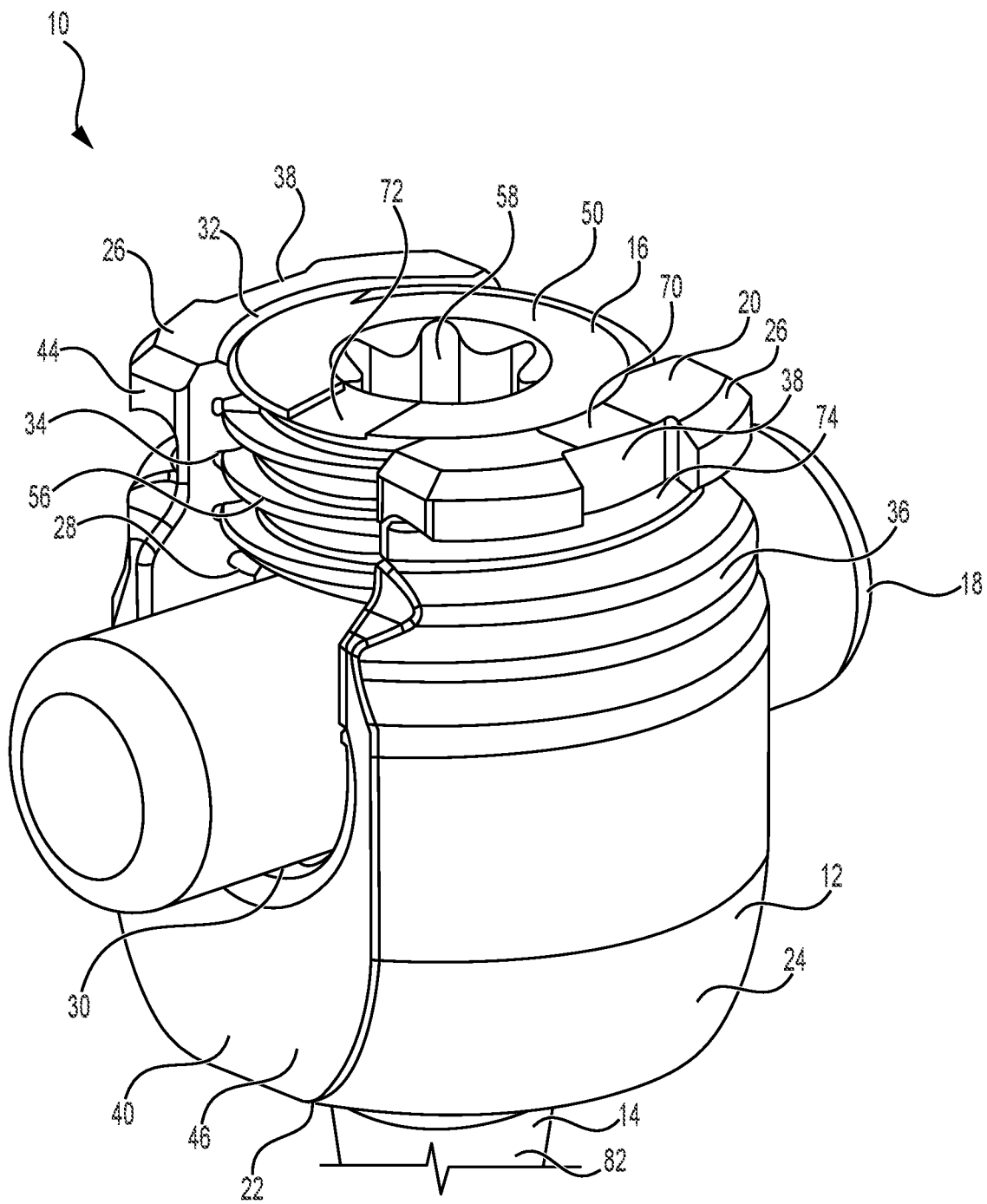
FIG. 1 shows a partial perspective view of a tulip head retaining a spinal rod therein and secured by a threaded locking cap according to one embodiment.
Figure 2:
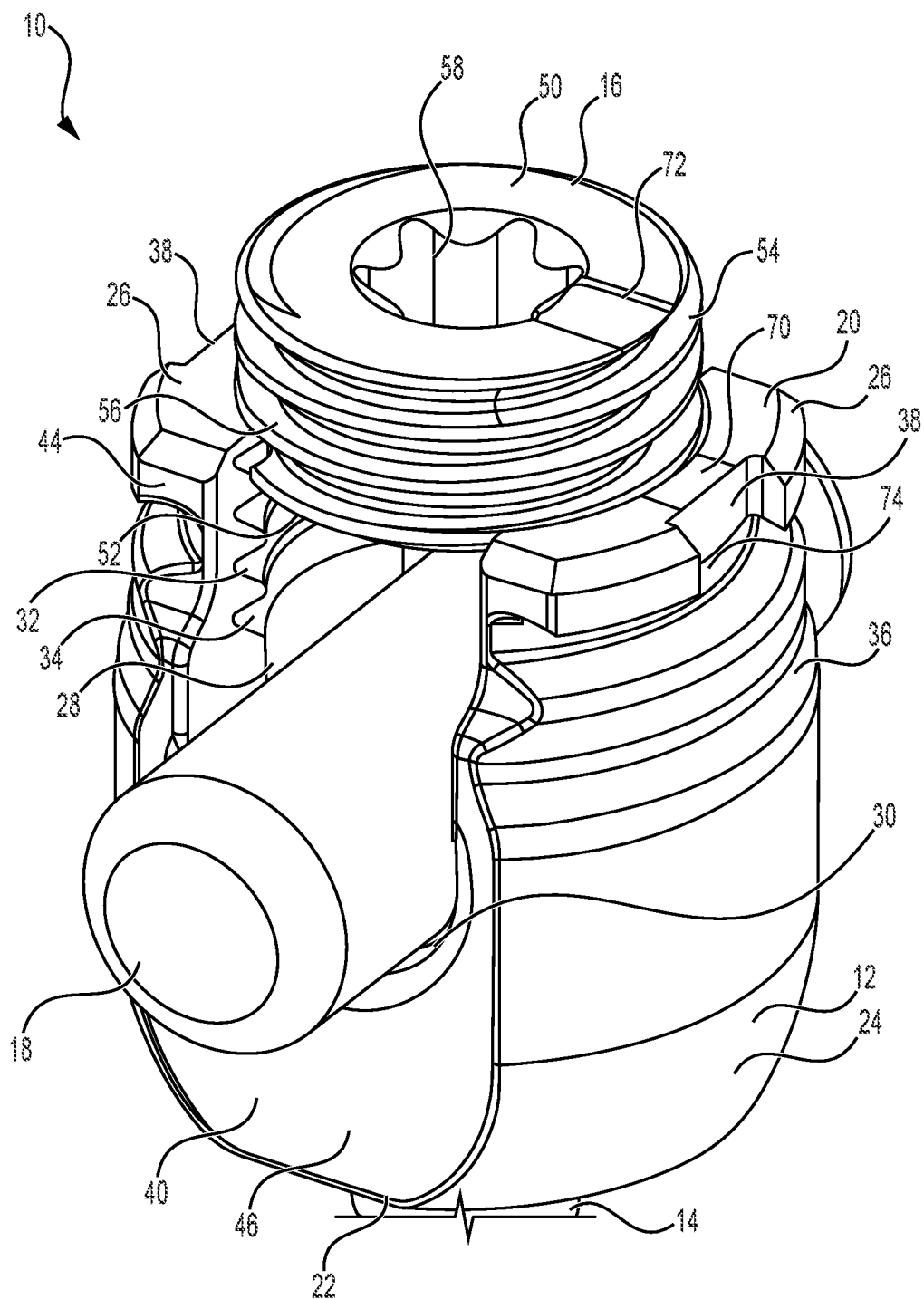
FIG. 2 shows a partial perspective view of the tulip head of FIG. 1 with the threaded locking cap in an upward position with indicators for beginning to thread the locking cap.
Figure 3:
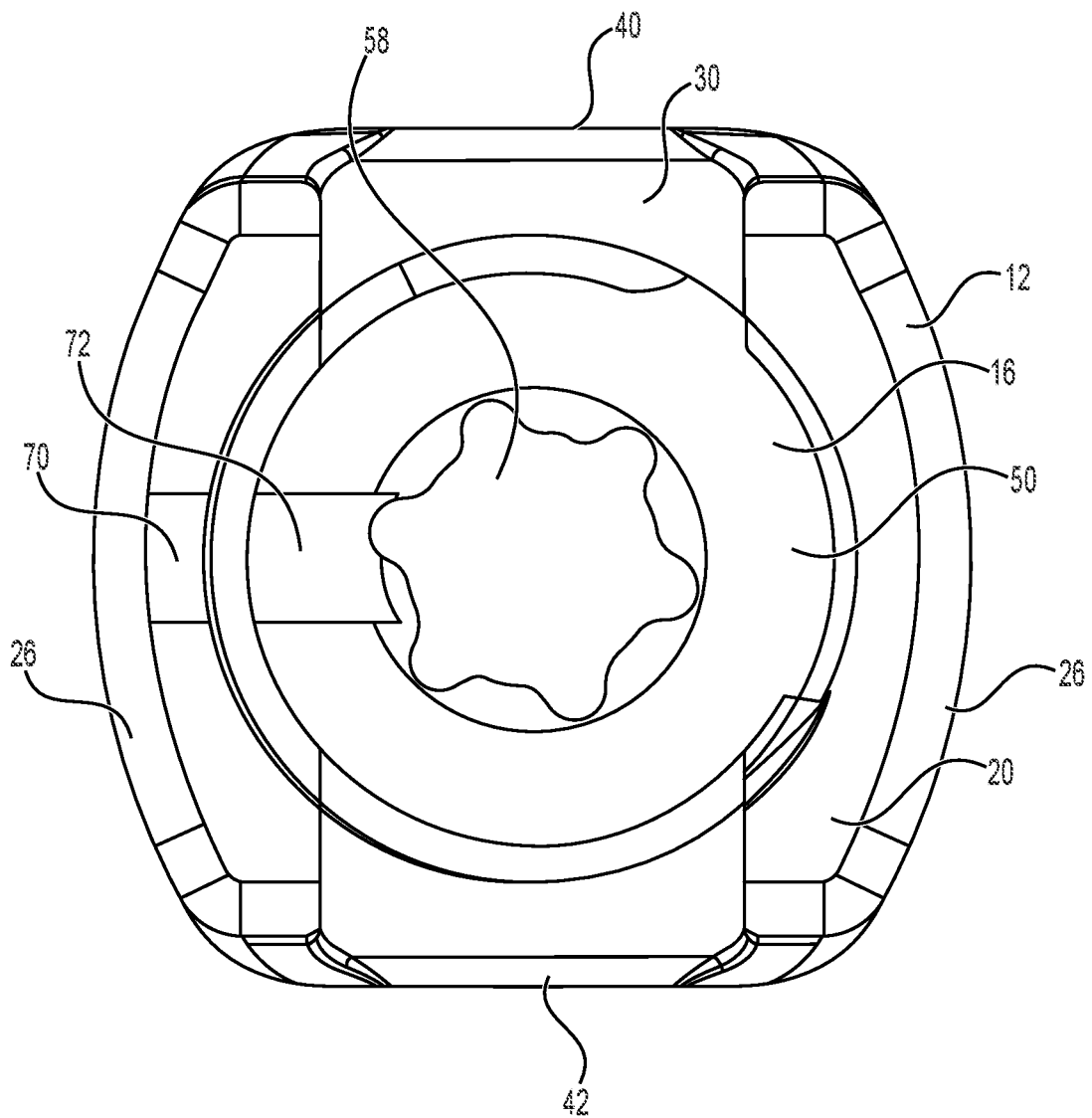
FIG. 3 shows a top view of the locking cap and tulip head with indicators according to one embodiment.

Referring now to FIGS. 1-3, an orthopedic fixation device, implant, or bone fastener assembly 10 is shown according to one embodiment. The bone fastener assembly or implant 10 may include a tulip element or tulip head 12, a bone fastener 14, and a locking cap 16 for securing a spinal rod 18 in the tulip head 12. For a polyaxial bone fastener 14, tightening the locking cap 16 compresses the rod 18 into the tulip head 12, thereby restricting motion of the bone fastener 14 and forming a rigid construct.

The tulip head 12 may extend from an upper surface or top 20 to a lower surface or bottom 22. The tulip head 12 may include a body 24 and arms 26 that extend upwardly from the body 24. A central bore 28 may extend through the body 24 of the tulip head 12. The opposed arms 26 may define a U-shaped channel or rounded rod slot 30, transverse to the bore 28. The rounded rod slot 30 is sized and configured to accept the rod 18. The rod slot 30 may be oriented perpendicular to the threads 56 of the locking cap 16. Each of the arms 26 has an interior surface 32 having a threaded portion 34 for engaging the locking cap 16. Each of the arms 26 may include an outer surface 36. The outer surface 36 of each of the arms 26 may include one or more tool engagement grooves 38 formed on the outer surface 36 which may be used for holding the tulip head 12 with a suitable tool (not illustrated). The sides of the tulip head 12 may define concentric diameters which taper towards the bottom 22 of the tulip head 12. The concentric diameters may have a smaller diameter at the top 20 of the tulip head 12, or may be a single diameter across the part. Front and back surfaces 40, 42 of the tulip body 24 may be planar or flat, with an upper flat 44 narrower in width than a lower flat 46. The flats 44, 46 and/or grooves 38 may act as one or more counter-rotation features when engaged with an instrument.

Figure 5:
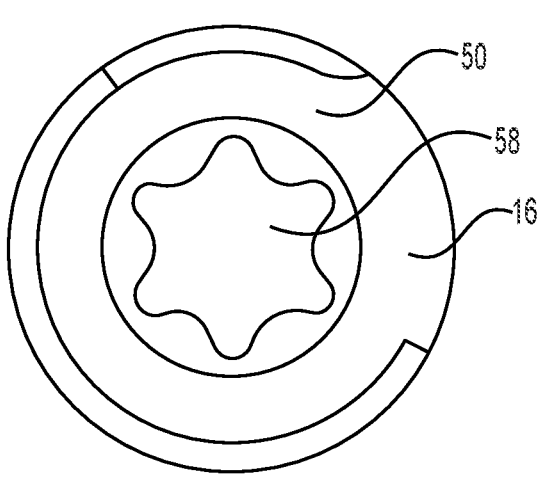
FIG. 5 is a top view of the threaded locking cap.

The rod 18 may be secured in the tulip head 12 with the locking cap 16. The locking cap 16 may include a body with an upper surface 50, a lower surface 52, and an outer body 54 defining a threaded portion 56. With emphasis on FIG. 5, the locking cap 16 may be in the form of a set screw with a drive feature or recess 58 defined in the upper surface 50. The drive recess 58 is configured to be engaged by a driving instrument, which is able to insert and tighten the locking cap 16 in the tulip head 12. The recess 58 may be a hexalobe, slot, cross, or other suitable shape that may engage with a tool or instrument having a corresponding tip. The recess 58 may extend partway into the body of the locking cap 16 or entirely through the locking cap 16. The bottom 52 of the locking cap 16 may be flat or otherwise configured to ensure consistent contact with the rod 18. The threaded portion 56 may extend between the upper and lower surfaces 50, 52 or a portion thereof.

Figure 4:
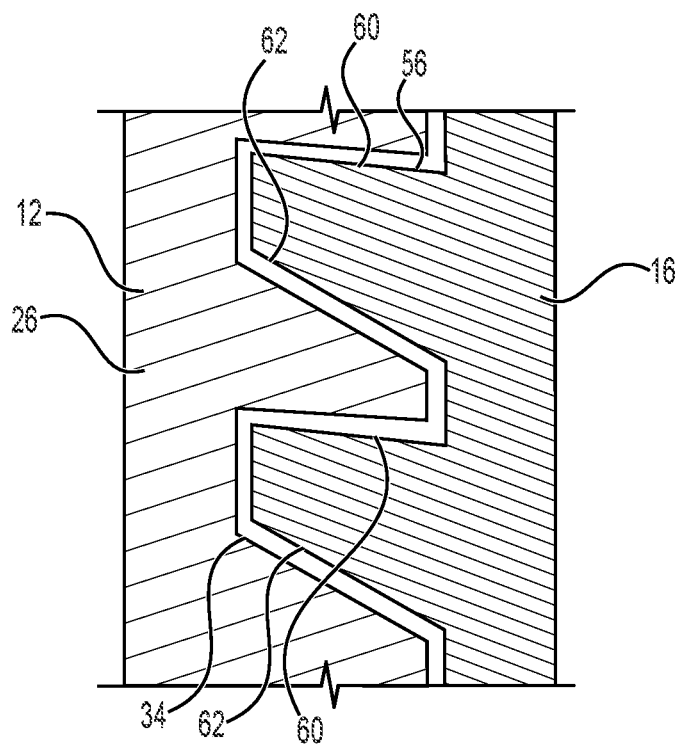
FIG. 4 is a close-up cross-sectional view of the threaded locking cap engaged with the tulip head.
Figure 6:
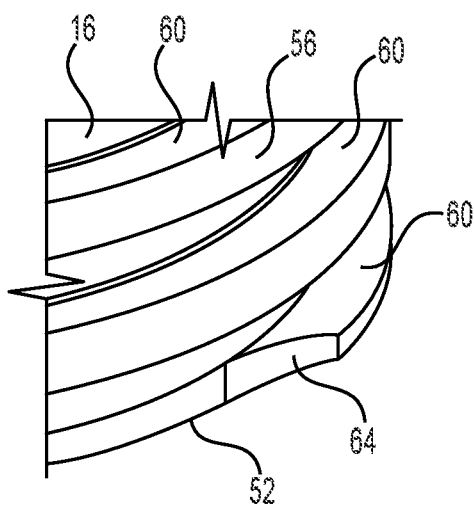
FIG. 6 is a close-up partial perspective view of the bottom of the threaded locking cap.
Figure 7:
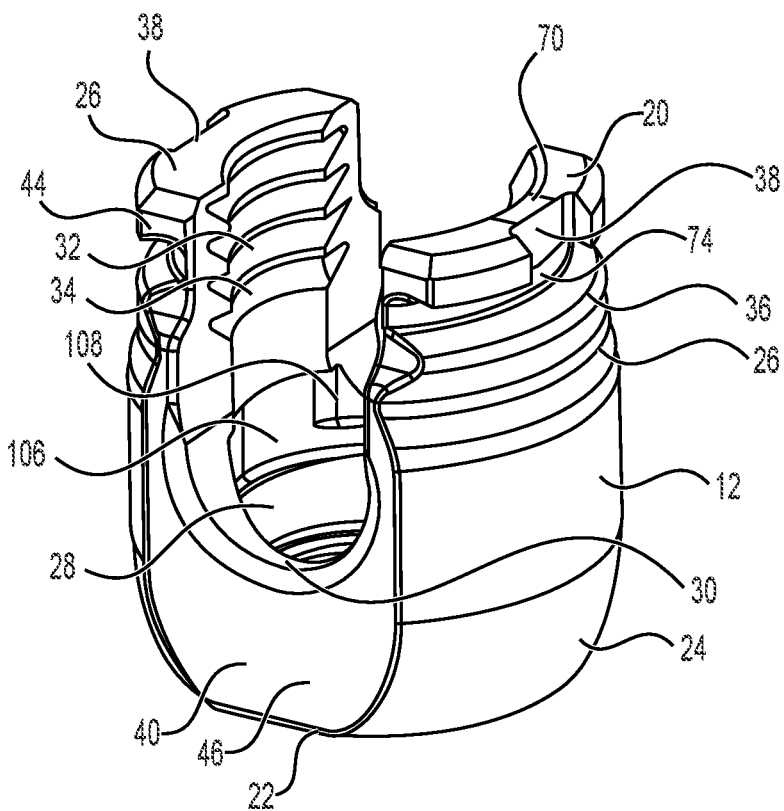
FIG. 7 shows a perspective view of the tulip head according to one embodiment.

As best seen in FIG. 4, the threaded portion 56 of the locking cap 16 may have a thread geometry configured to secure the locking cap 16 to the tulip head 12. The locking cap thread geometry may form a buttress section with an inward top. For example, a top surface 60 of the locking cap thread may be angled inward, towards the minor diameter, and a bottom surface 62 of the locking cap thread may be angled outward away from the minor diameter. With emphasis on FIG. 6, the first thread beginning at the bottom 52 of the locking cap 16 may be broken by a radiused cut 64 to increase the strength of the first thread as it is being engaged with the tulip head 12 and/or to prevent cross-threading of the locking cap 16. The locking cap 16 may include a thread geometry that improves strength, reduces outward splaying forces on the tulip head 12, increases resistance to cross-threading, allows quick engagement of the locking cap 16, and/or maintains a more consistent interface with mating instruments. Although a threaded locking cap 16 is exemplified herein, it will be appreciated that a non-threaded cap or other suitable locking cap may be selected to secure the rod 18 and/or the bone fastener 14.

The tulip head 12 and/or locking cap 16 may include one or more indicators 70, 72 to show the best alignment to start threading the locking cap 16 into the tulip head 12, for example, to help avoid off angle insertion. By way of example, each of the indicator(s) 70, 72 may include one or more laser marks, grooves, cutouts, protrusions, or other visual features configured to align a relative starting position of the locking cap 16 to the tulip head 12. As best seen in FIG. 3, in one embodiment, a first indicator 70 may be provided on the tulip head 12. For example, the first indicator 70 may include at least one laser mark on the upper surface 20 of one arm 26 of the tulip head 12. The laser mark indicator 70 may include one or more lines (e.g., two parallel lines) extending from the inner surface 32 to the outer surface 36 of one of the arms 26. A second indicator 72 may be provided on the locking cap 16. For example, the second indicator 72 may include a groove and/or laser mark on the top surface 50 of the locking cap 16. The second indicator 72 (e.g., groove and/or laser mark) may also include a groove defined between one or more lines (e.g., two parallel lines) extending radially from the recess 58 to the outer surface 54 of the locking cap 16. As shown in FIG. 2, a third indicator 38 may be provided on the tulip head 12. The third indicator 38 may include one of the slots or cutouts 38 in the side of one of the arms 26. The slot or cutout 38 may be aligned with the laser mark indicator 70 on the top 20 of the arm 26. The indicators 70, 72 may help to align the tulip head 12 and locking cap 16 before threading, in order to help avoid off angle insertion of the locking cap 16.

The starts of the threads 34, 56 in the locking cap 16 and tulip head 12 may be timed with the corresponding indicators on the locking cap 16 and/or tulip head 12. As shown in FIG. 2, when the indicators (e.g., marking 70, groove 72, and/or cutout 38) are aligned, the start of the thread 54 on the locking cap 16 is close to engaging the thread 34 on the tulip head 12. The first thread of the threaded portion 56 of the locking cap 16 may be timed to the indicators on the locking cap 16 and tulip head 12, thereby acting as alignment indicators to allow quick alignment and engagement of the first thread. When the indicators 70, 72 are aligned (e.g., the lines of the laser mark 70 are aligned with the groove 72), the locking cap 16 is able to sit flat and be immediately engaged with the tulip head 12. This may help to avoid off angle insertion of the locking cap 16 into the tulip head 12. The indicators 70, 72 may allow the user to quickly and repeatably engage the threads 34, 56 of the locking cap 16 with the tulip 12.

The bone fastener 14 may include a bone screw, anchor, clamp, or the like configured to engage bone. In one embodiment, the bone fastener 14 is a bone screw, such as a polyaxial pedicle screw, having a screw head 80 and a threaded shaft 82 that extends from the screw head 16. Suitable bone fasteners 14 will be recognized by those of ordinary skill in art. Examples of bone fasteners and other implants and rod constructs are described in more detail, for example, in U.S. Pat. No. 10,368,917, which is incorporated by reference herein in its entirety for all purposes. It will be appreciated that the threaded shaft 82 may have a number of different features, such as thread pitch, shaft diameter to thread diameter, overall shaft shape, and the like, depending, for example, on the particular application. While the screw head 80 may have any general shape, in the case of a polyaxial fastener 14, at least a portion of the screw head 80 may have a curved surface in order to allow for rotational movement and/or angular adjustment of the bone fastener 14 with respect to the tulip head 12. For example, at least a portion of the screw head 80 may be shaped to form a portion of a ball or at least a portion of a sphere. The screw head 80 may have a tool engagement surface 84, for example, that can be engaged by a screw-driving instrument or other device. In one embodiment, the screw head 80 has a hexalobe recess 84 for driving the screw 14 into bone. It will be appreciated that any suitably shaped tool engagement surface 84 may be provided. Although a polyaxial bone screw is exemplified herein, it will be appreciated that the fastener may be substituted with uniplanar, monoaxial, reduction, modular, or other suitable fasteners.

The polyaxial mechanism may be a spherical joint between a spherical head 80 of the bone screw 14, the tulip head 12, and a saddle 90. The saddle 90, positioned within the bore 28 of the tulip head 12, may provide a collar about an upper portion of the screw head 80. The polyaxial motion of the bone fastener 14 may be locked when the locking cap 16 is threaded downwardly, compressing the rod 18 onto the saddle 90, which thereby compresses against the spherical head 80 of the bone screw 14. Thus, the locking cap 16 is able to lock the position of the bone fastener 14 and the rod 18, thereby forming a rigid construct.

Figure 8:
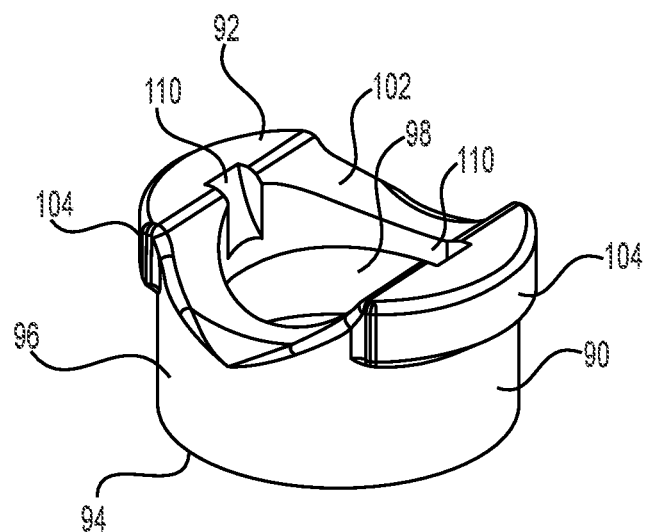
FIG. 8 shows a perspective view of a saddle, configured to rotate into engagement with the tulip head, according to one embodiment.

In one embodiment shown in FIG. 8, the saddle 90 may include an upper surface 92, a lower surface 94, an outer surface 96, which may be curved or rounded, and a bore 98 defined through the saddle 90. A lower portion of the bore 98 may be rounded and sized to receive an upper portion of the screw head 80. A rod slot or seat 102 may be defined in the upper surface 92 of the saddle 90. The rod slot or seat 102 may be configured to receive a bottom portion of the rod 18 therein. The saddle 90 may include one or more external lips or wings 104. For example, the saddle 90 may include two opposed, outwardly extending wings 104 positioned at the top 92 of the saddle 90.

Figure 9:
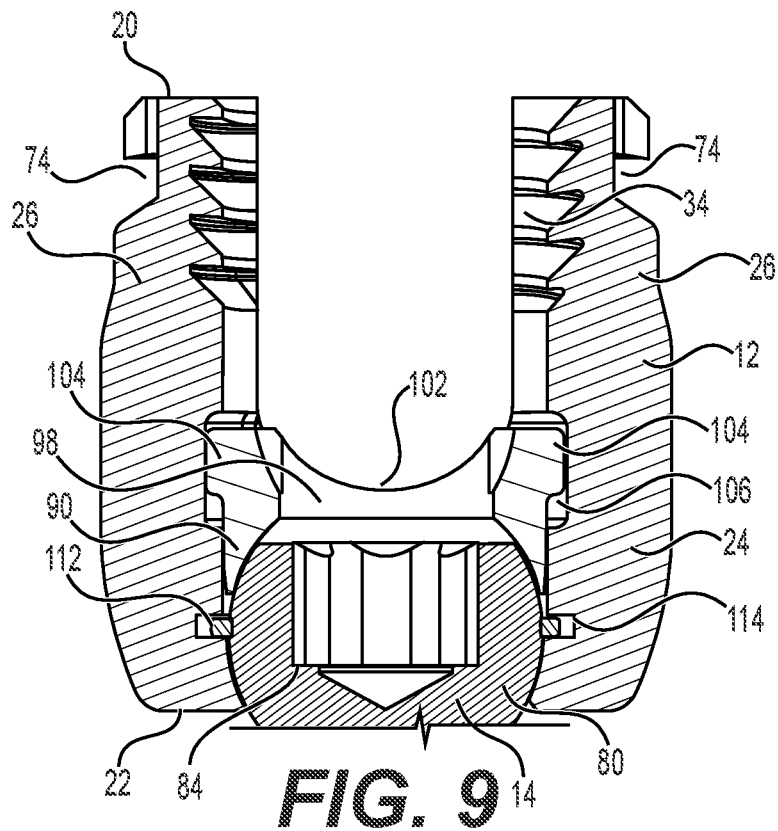
FIG. 9 shows a partial cross-sectional view of an assembly including a split ring for applying compression to the screw head according to one embodiment.
Figure 10:
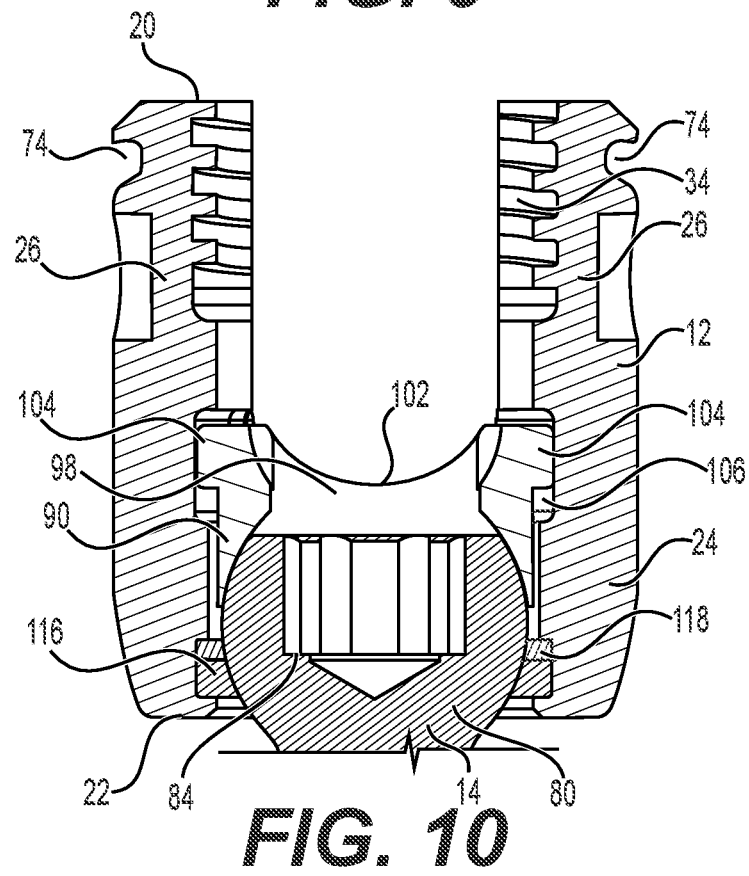
FIG. 10 shows a partial cross-sectional view of an assembly including a clip for retaining the screw head within the tulip head according to one embodiment.

As shown in FIGS. 9 and 10, the wings 104 may be configured to be received in one or more corresponding recesses or grooves 106 in the tulip head 12. The saddle 90 may be rotatable within the tulip head 12 in order to engage the saddle 90 within the recesses or grooves 106. For example, the saddle 90 may be inserted from the top 20 of the tulip head 12 with the seat 102 rotated out of alignment with the rod slot 30 of the tulip head 12. After insertion into the tulip head 12, the saddle 90 may be rotated about the central longitudinal axis A and into alignment with the internal groove 106 in the tulip head 12. In one embodiment, the saddle 90 may be first inserted in a first initial orientation with the seat 102 at about 90° offset relative to its final position, and then subsequently rotated 90° to a second final orientation with the seat 102 substantially aligned with the U-shaped rod slot 30 between the arms 26 of the tulip head 12.

A portion of the saddle 90 (e.g., the upper profile of the wings 104) and internal groove 106 of the tulip head 12 may be elliptically shaped to prevent the saddle 90 from inadvertently rotating out of alignment. One or more relief cuts 108 may be provided in the tulip head 12 to allow rotation of the saddle 90 into alignment only in one direction. Thus, the saddle 90 may only be twisted or rotated in a single direction for engagement with the inner groove 106. One or more grooves or engagement recesses 110 may be cut into the saddle 90 to allow for an interface with an assembly tool to facilitate rotation of the saddle 90. For example, opposed engagement recesses 110 may be provided within the upper surface 92 on opposite sides of the bore 98, which allows for a tool (not shown) to rotate the saddle 90 into position.

With emphasis on FIGS. 9-12, the screw head 80 may be further retained in the tulip head 12 by a split ring 112, a clip 116, an internal taper 120, or other suitable mechanism configured to retain the screw head 80 in the body 24 of the tulip 12. In one embodiment shown in FIG. 9, a split ring 112 may be housed within an internal groove 114 of the tulip head 12. The split ring 112 may include a ring with a central through opening and a cut in fluid communication with the central through opening. The split ring 112 may optionally sit in a corresponding groove in the head 80 of the screw 14. The split ring 112 may apply a compression to the screw head 80, providing a consistent friction to the polyaxial joint to retain the position of the screw 14.

In one embodiment shown in FIG. 10, the polyaxial mechanism may utilize a clip 116 to retain the screw 14 within the tulip head 12. The clip 116 may be received within an internal groove 118 in the tulip head 12. The clip 116 may be located at a bottom portion of the tulip head 12 beneath the widest part of the screw head 80. With the clip 116, the spherical head 80 of the bone screw 14 may be inserted into the tulip head 12 and the clip 116 inserted into the internal groove 118 of the tulip head 12 to retain the bone screw 14 therein. In this manner, the bone fastener 14 is prevented from separating from the tulip head 12.

Figure 11:
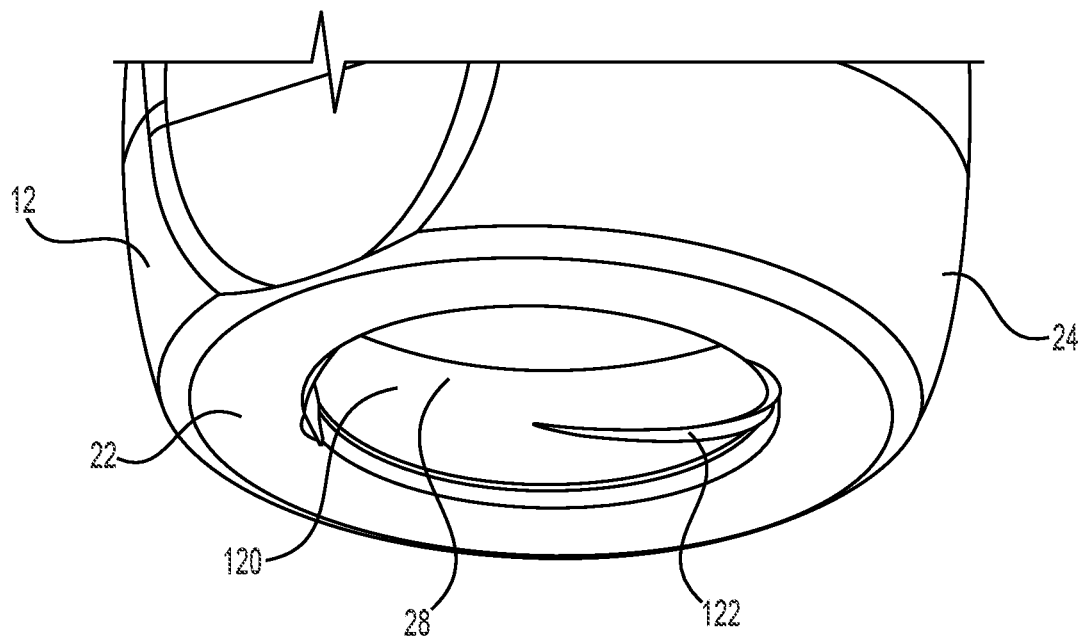
FIG. 11 is a partial bottom perspective view of the tulip head according to one embodiment.
Figure 12:
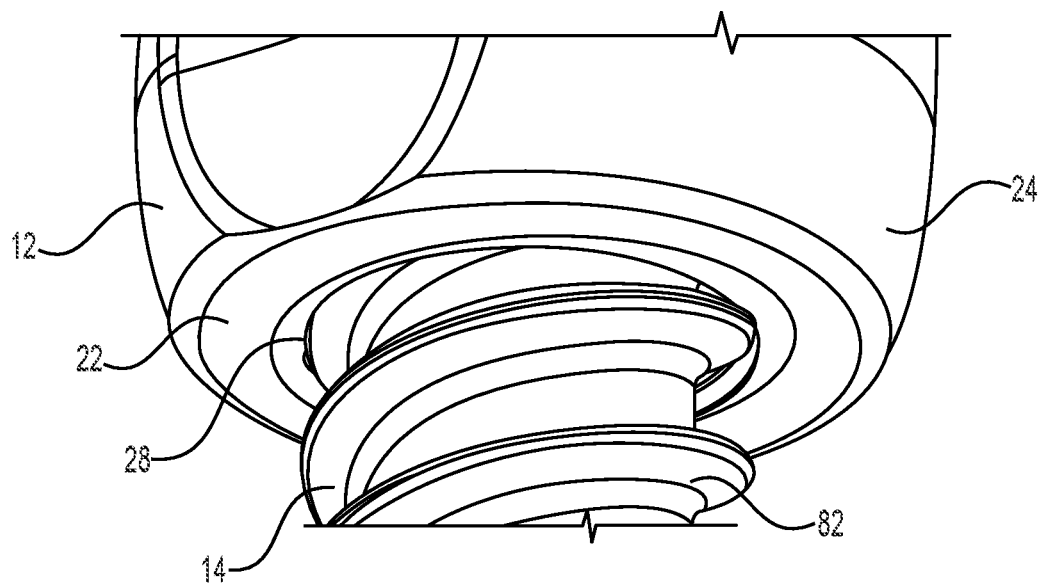
FIG. 12 is a partial bottom perspective view of the tulip head with a bone fastener positioned therethrough.

In one embodiment shown in FIGS. 11-12, the screw head 80 may be positioned within the bore 28 in the tulip head 12 and prevented from disengaging from the tulip head 12 by an internal taper 120 within the tulip head 12. The screw 14 may be inserted from the top 20 of the tulip head 12 until the screw head 80 contacts the taper 120 at the bottom 22 of the tulip head 12. The saddle 90 may be inserted from the top 20 of the tulip head 12 and then rotated into alignment with the rod slot 30 of the tulip head 12. One or more threads 122 may be cut into the taper 120 at the bottom 22 of the tulip head 12. The thread(s) 122 in the internal taper 120 may be shaped to allow the largest screw possible to thread through the assembly. The tapered tulip reduces the total number of components and simplifies assembly, but limits the largest screw size that may be assembled through the tulip 12.

Figure 13:
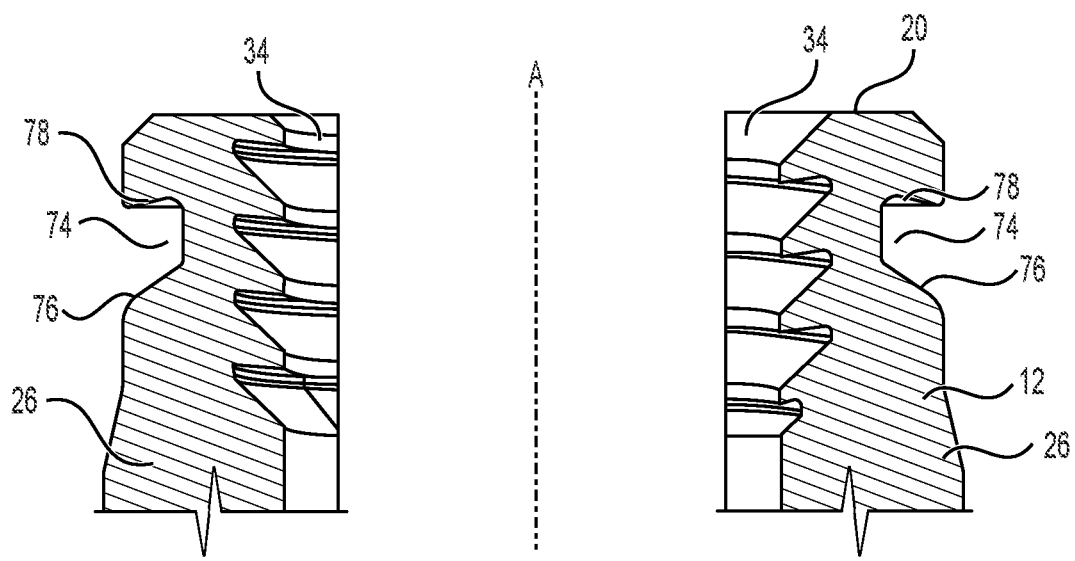
FIG. 13 shows a partial cross-sectional view of the arms of the tulip head configured to receive the threaded locking cap according to one embodiment.
Figure 14:
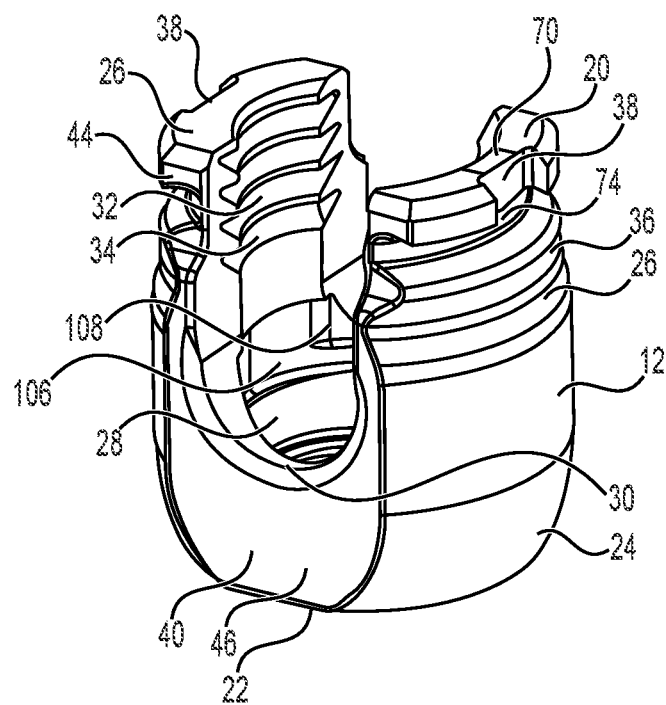
FIG. 14 is a perspective view of the tulip head according to one embodiment.

Turning now to FIGS. 13-14, one or more instrument interfaces may be used for engaging one or more instruments, such as insertion, positioning, reduction, and/or derotation instruments. The instrument interfaces may be engaged by instruments, for example, with tabs or grooves similarly shaped to the reduction features which collapse, pivot, slide, or flex into engagement with the tulip head 12. For example, an annular or cylindrical groove 74 may be cut into the outer diameter of the tulip head 12 for engagement of insertion, reduction, derotation, compression, distraction and/or other holding instruments. The exterior groove 74 may form a single reverse angle groove section. For example, an upward-facing surface 76 of the cylindrical groove 74 may be angled outwards away from the central longitudinal axis A of the tulip head 12, while a downward-facing surface 78 of the cylindrical groove 74 may be angled inwards toward the central axis A. The inward angle of the downward-facing surface 78 may help to prevent disengagement of the instrument under load by directing forces downward and towards the central axis A of the tulip head 12.

The locking cap threads 56 may also be engaged with the tulip threads 34 to axially constrain the implant 10. The cylindrical groove 74 and threads 34, 56 allow the central axis A of the implant 10 to be constrained to the central axis of an instrument. To constrain rotation, one or more slots 38 (e.g., two opposed slots) may be cut into the outer diameter of the arms 26 which allows engagement of an instrument to prevent rotation. In addition or alternatively, an instrument may prevent rotation against the upper and lower flats 44, 46. The instrument interfaces allow instruments to fully or partially constrain or attach to the implant, provide increased holding strength, decrease splaying forces which may cause disengagement of instruments, and/or simplify manufacturing.

Figure 15:
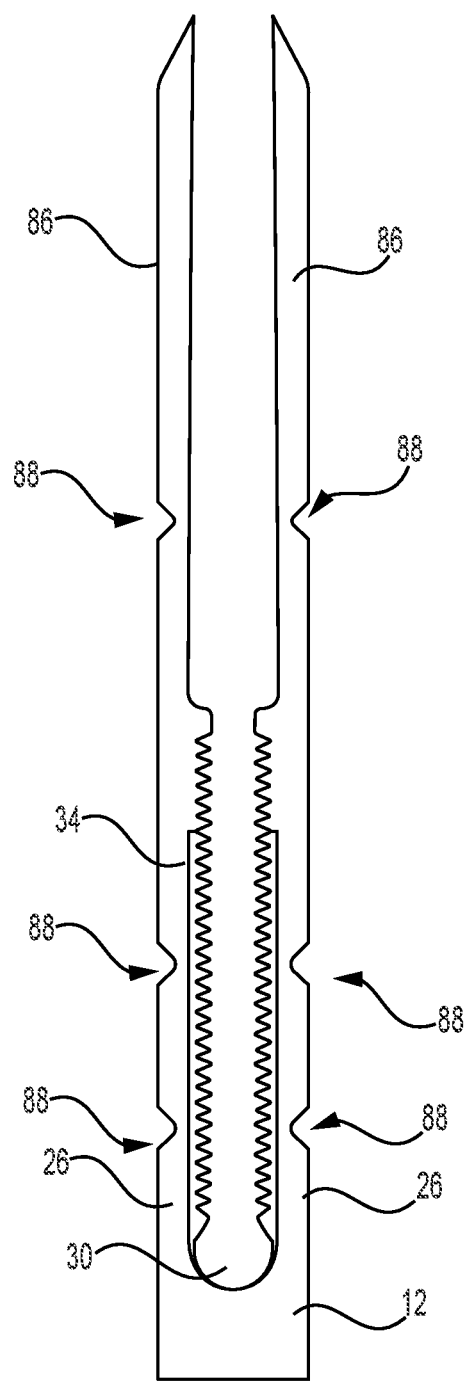
FIG. 15 is an embodiment of a tulip head with removable reduction tabs.

Turning now to FIG. 15, the arms 26 of the tulip head 12 may be extended to provide adjustable length reduction tabs 86. For example, extensions or extended tabs 86 may be provided to each of the arms 26. The threaded upper portion 34 of the tulip head 12 may be extended along a portion or the entire extended tabs 86 to allow the rod 18 to be captured and reduced into the tulip head 12 by downwardly threading the locking cap 16. The extended tabs 86 may be removable at one or more breaking points 88. Each breaking point 88 may be provided as an internal and/or external groove, for example, which allows for the extended tabs 86 to be broken away from the tulip head 12 once they are no longer needed. In this embodiment, multiple breaking points 88 may be included at multiple heights to allow the user to break the tabs 86 at a desired height to reduce the amount of turns necessary to turn the locking cap 16 and/or prevent contact with adjacent implants. The reduction tabs 86 may allow for additional intraoperative adaptability when reducing the rod 18 into the tulip head 12.

Figure 16:
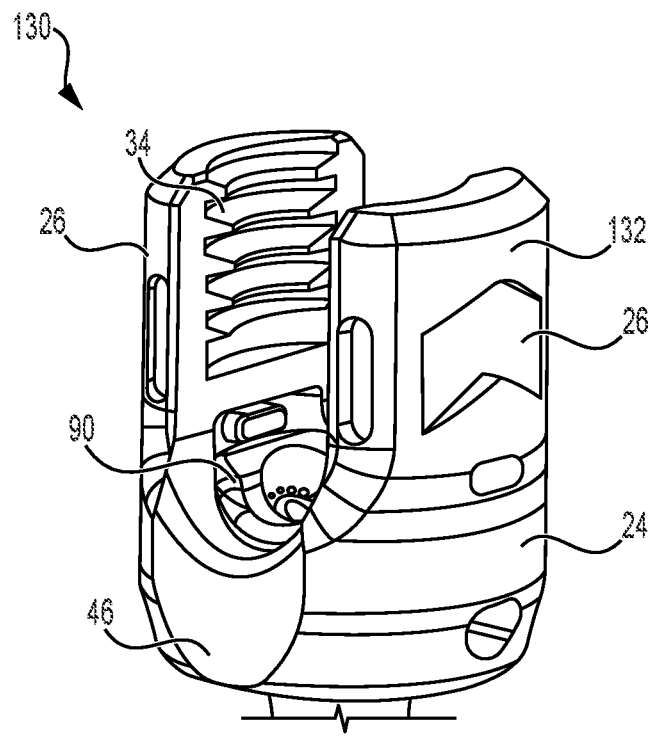
FIG. 16 shows a partial perspective view of an embodiment of a tulip assembly configured for retaining a uniplanar screw.
Figure 17:
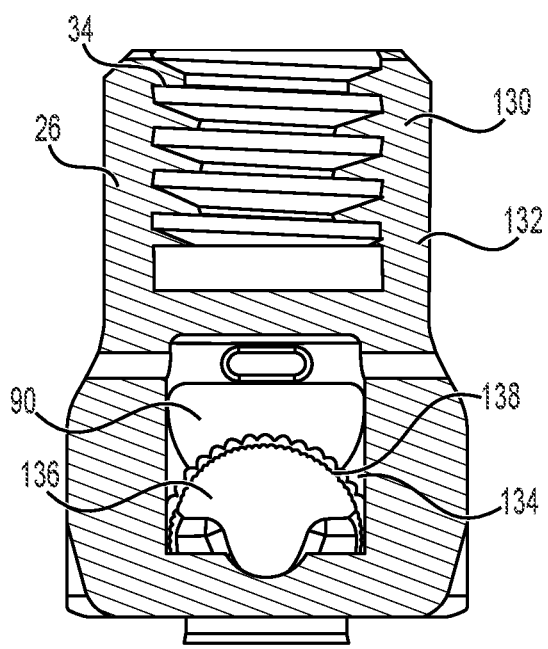
FIG. 17 is a partial cross-sectional view of the uniplanar assembly of FIG. 16.
Figure 18:
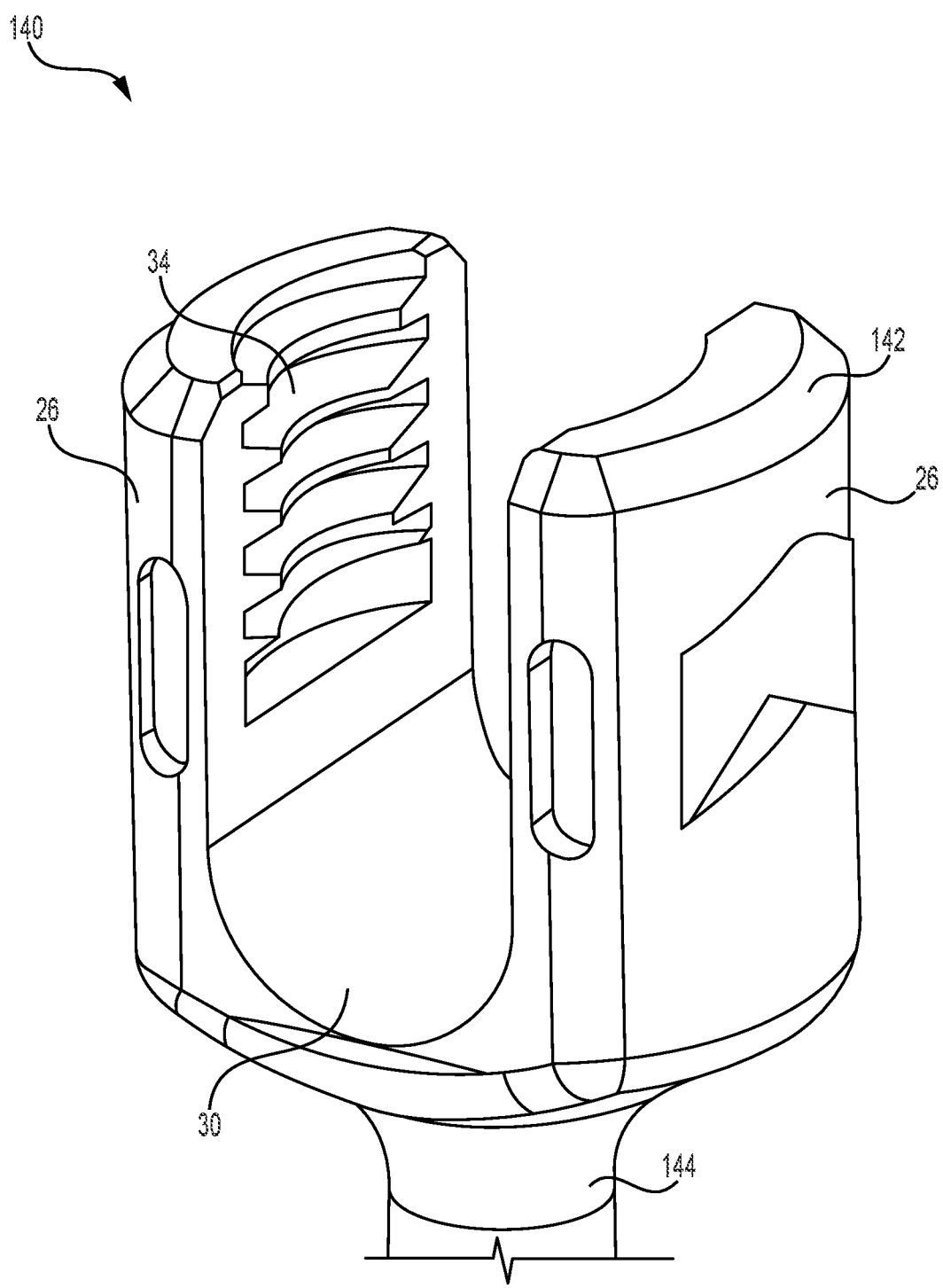
FIG. 18 shows a partial perspective view of an embodiment of a monoaxial fastener.

Turning now to FIGS. 16-18, the tulip head 12 may also be applied to other screw designs, such as uniplanar and monoaxial screws. FIGS. 16 and 17 show an embodiment of a uniplanar screw assembly 130 (a close-up of the tulip 132 is shown with a portion of the screw shaft omitted for clarity). Similar to the polyaxial screw assembly 10, the uniplanar screw assembly 130 includes a tulip head 132 and a saddle 90 for retaining a screw head 136 of a uniplanar screw. The uniplanar tulip 132 includes a through hole 134 which accepts the screw head 136. For a uniplanar screw, the tulip head 12 pivots on the screw head 132 in only one direction. The tulip head 12 may be permitted to pivot either along the rod slot 30 or perpendicular to the rod slot 30 depending on the orientation of the through hole 134 and screw head 136. Similar to the polyaxial screw 10, the saddle 90 compresses against the head 136 of the screw when a threaded locking cap 16 is threaded downwardly onto the spinal rod 18, thereby pushing against the saddle 90. In this locked position, the uniplanar screw assembly 130 is locked in place, thereby restricting motion and locking the position of the uniplanar screw. A plurality of teeth, groove cuts, or a roughened surface 138 on the screw head 136 and/or saddle 90 may increase the grip strength of the interface between the screw head 136 and the bottom of the saddle 90.

FIG. 18 shows an embodiment of a monoaxial screw 140 (a close-up of the tulip 142 is shown with a portion of the screw shaft omitted for clarity). Similar to the polyaxial screw assembly 10, the monoaxial screw 140 includes a tulip head 142 for receiving a spinal rod 18. The monoaxial screw 140 combines the tulip head 142 with a bone screw shaft 144 into a single unitary component. A threaded locking cap 16 may be threaded downwardly onto the spinal rod 18, thereby securing the rod 18 in the rigid construct. The uniplanar and monoaxial screw designs allow for rigidity in various directions, which may allow the user to transmit forces to the vertebral body for correction or screw insertion.

Figure 19:
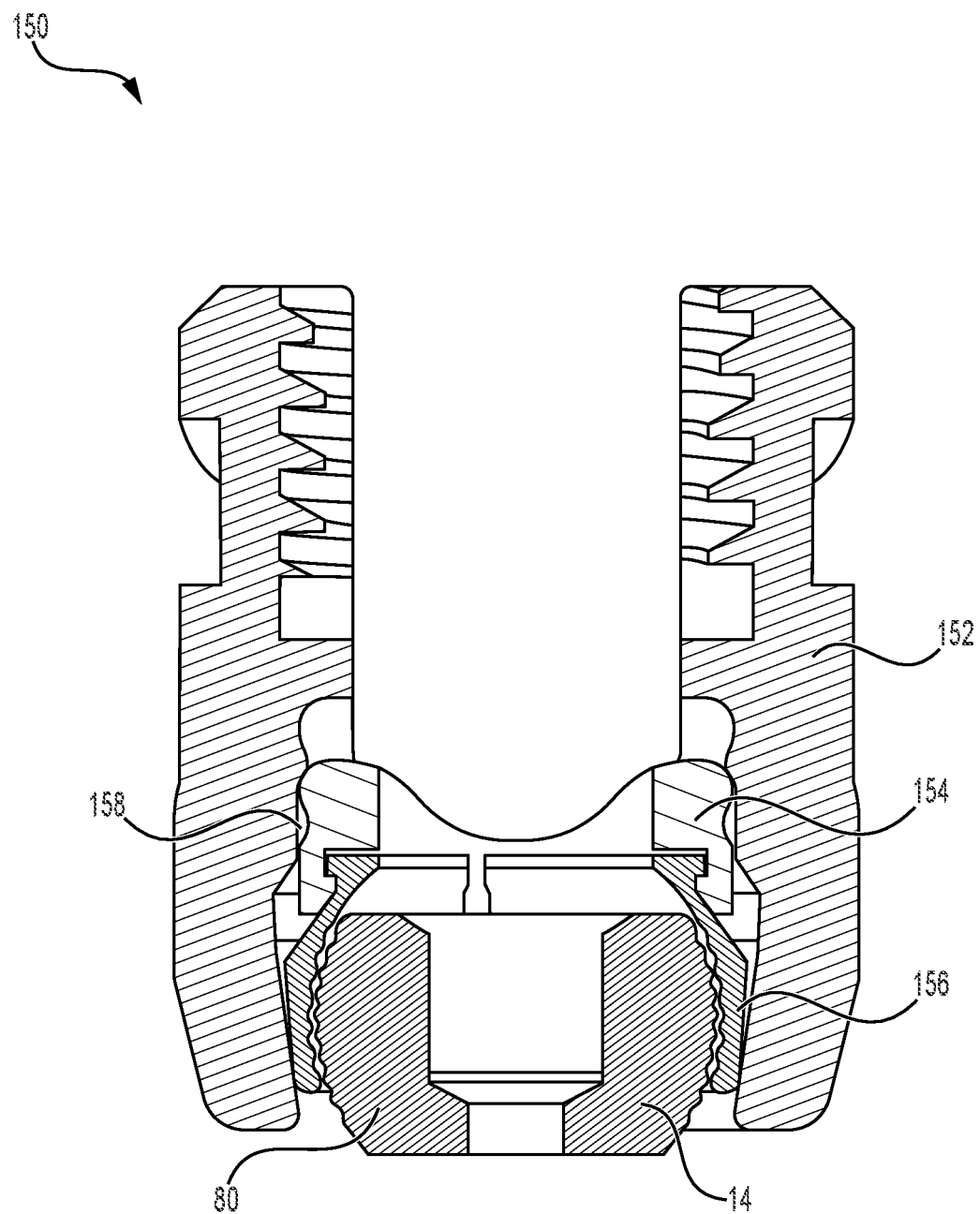
FIG. 19 shows a partial cross-sectional view of an embodiment of a tulip assembly with a saddle and clamp for retaining a screw head.

Turning now to FIG. 19, an embodiment of a preassembled polyaxial pedicle screw assembly 150 is shown. Similar to the polyaxial screw assembly 10, the polyaxial screw assembly 150 includes a tulip head 152, a saddle 154, and further includes a clamp 156 for retaining the screw head 80 of the polyaxial screw 14. The saddle 154 is capable of translation across a modular bump 158. Similar assemblies are described in U.S. Pat. No. 10,368,917, which is incorporated by reference herein in its entirety for all purposes.

With emphasis on FIGS. 20-23, an embodiment of a preassembled polyaxial pedicle screw assembly 160 is shown. Assembly 160 is similar to assembly 150 except in this embodiment, assembly of the components is achieved via rotation and translation of an elliptical saddle 164 into an elliptical bore 192 of the tulip 162 in lieu of the translation of the saddle 154 across the modular bump 158. This different may ease assembly during production and prevent the saddle 164 from inadvertently translating back to an unlocked position.

Similar to implant 10, the polyaxial pedicle screw assembly 160 may include a tulip head 162, a rotatable saddle 164, a bone fastener 14, and a threaded locking cap 16 for securing the spinal rod 18 in the tulip head 162. The tulip head 162 may include a body 168 and arms 170 that extend upwardly from the body 168. A central bore 172 may extend through the body 168 of the tulip head 162. The opposed arms 170 may define a U-shaped channel or rod slot 174, transverse to the bore 168. The rounded rod slot 174 is sized and shaped to accept the rod 18 perpendicular to the threads of the locking cap 16. Each of the arms 170 has an interior surface defining a threaded portion 176 for engaging the threaded locking cap 16. Each of the arms 170 may include one or more tool engagement surfaces or recesses 178, which may be used for holding the tulip head 162 with a suitable tool (not illustrated). Front and/or back surfaces 180 of the tulip body 168 may be flat, for example, to allow for engagement of an instrument to prevent rotation of the tulip head 162. The rod 18 may be secured in the tulip head 12 with the threaded locking cap 16.

As shown in FIG. 22, the rotatable saddle 164 may include an upper surface 182, a lower surface 184, an outer surface 186, which may be curved or rounded, and a bore 188 defined through the saddle 164. A lower portion of the bore 188 may be rounded and sized to receive an upper portion of the clamp 166. A rod slot or seat 190 may be defined in the upper surface 182 of the saddle 164. The rod slot or seat 190 may be configured to receive a bottom portion of the rod 18 therein. The saddle 164 may be configured to be received in a recess or bore 192 in the tulip head 162.

Figure 20:
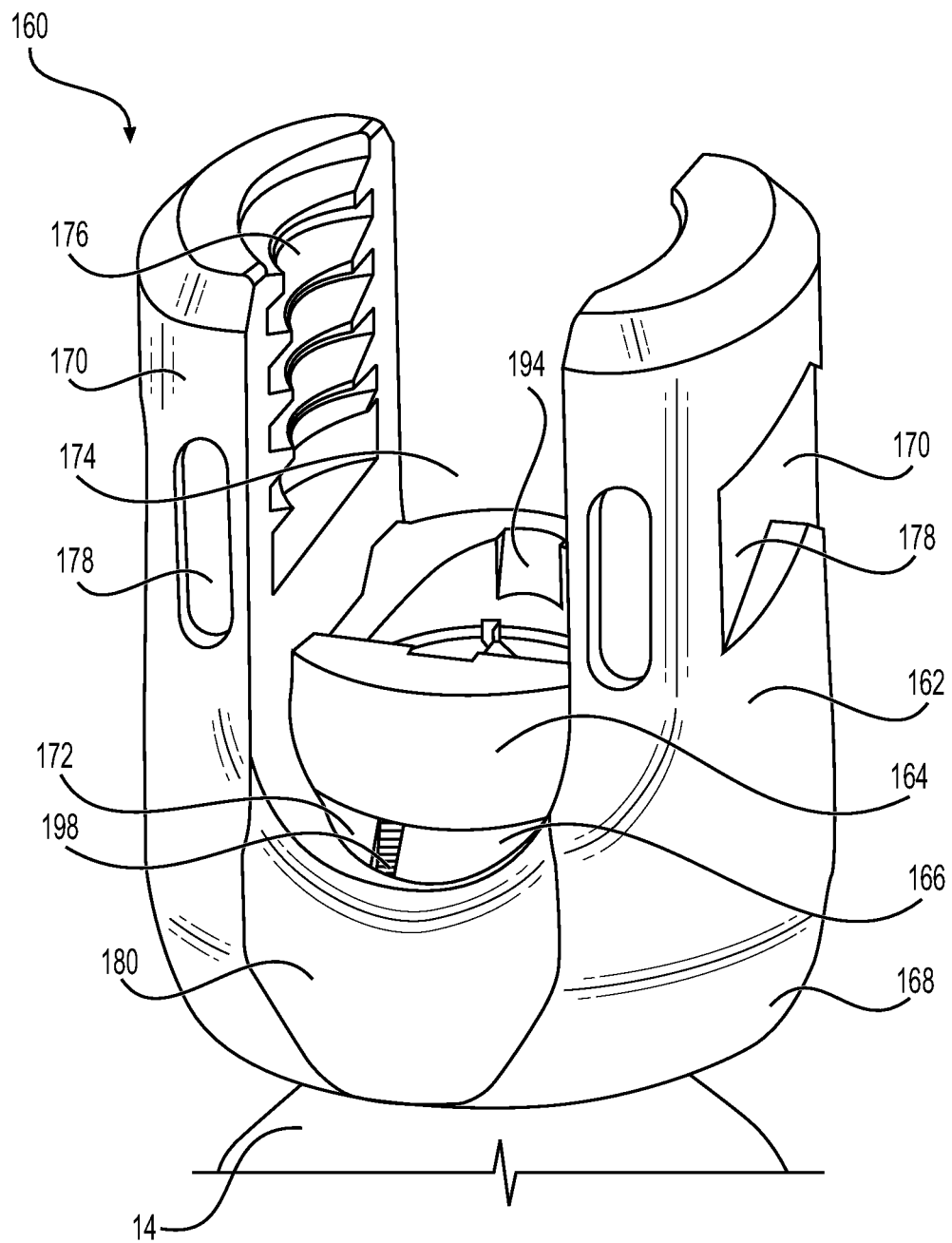
FIG. 20 shows a partial perspective view of a tulip assembly with a saddle in an upward unlocked position according to one embodiment.
Figure 21:
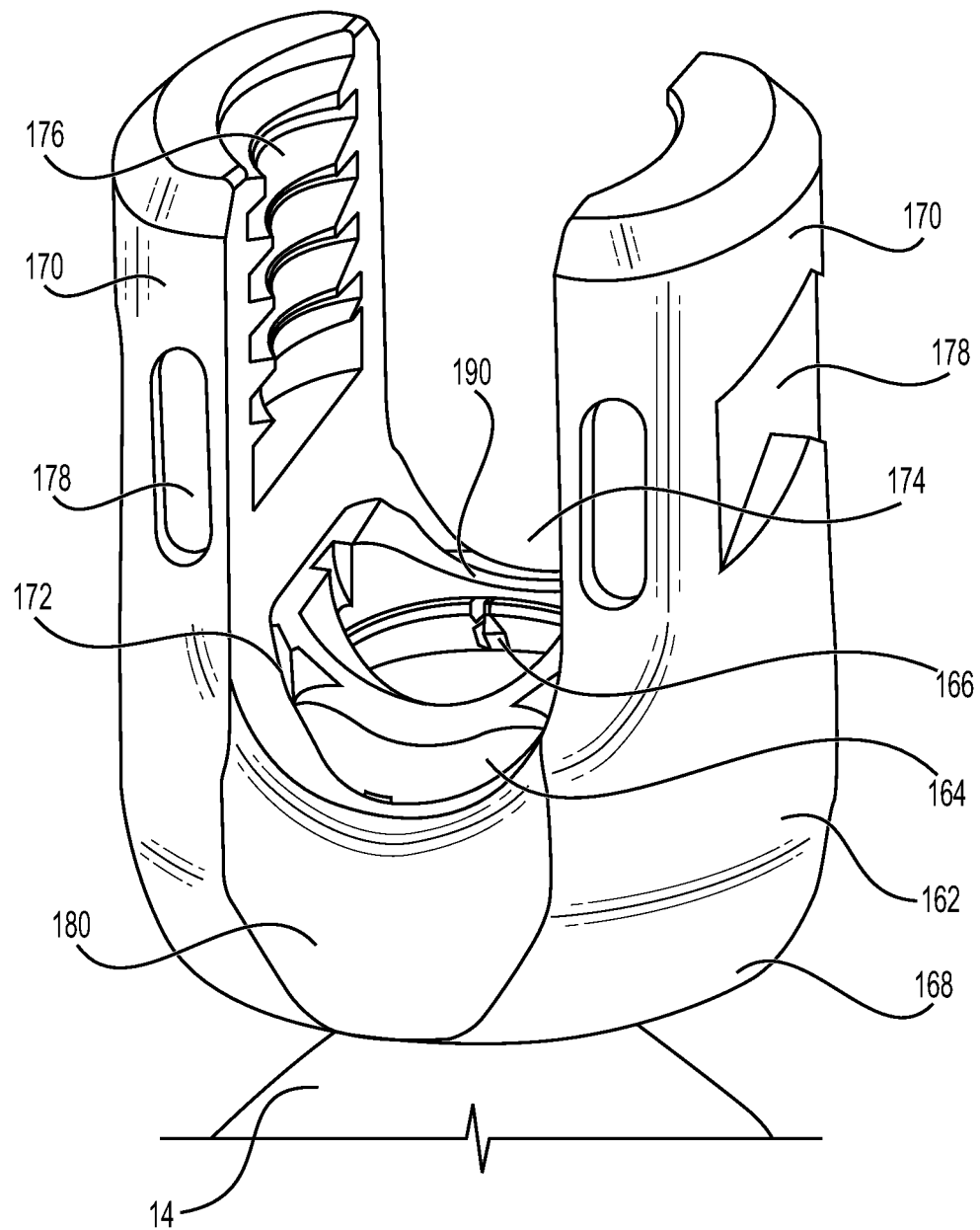
FIG. 21 shows a partial perspective view the tulip assembly of FIG. 20 with the saddle rotated in a downward locked position.
Figure 23:
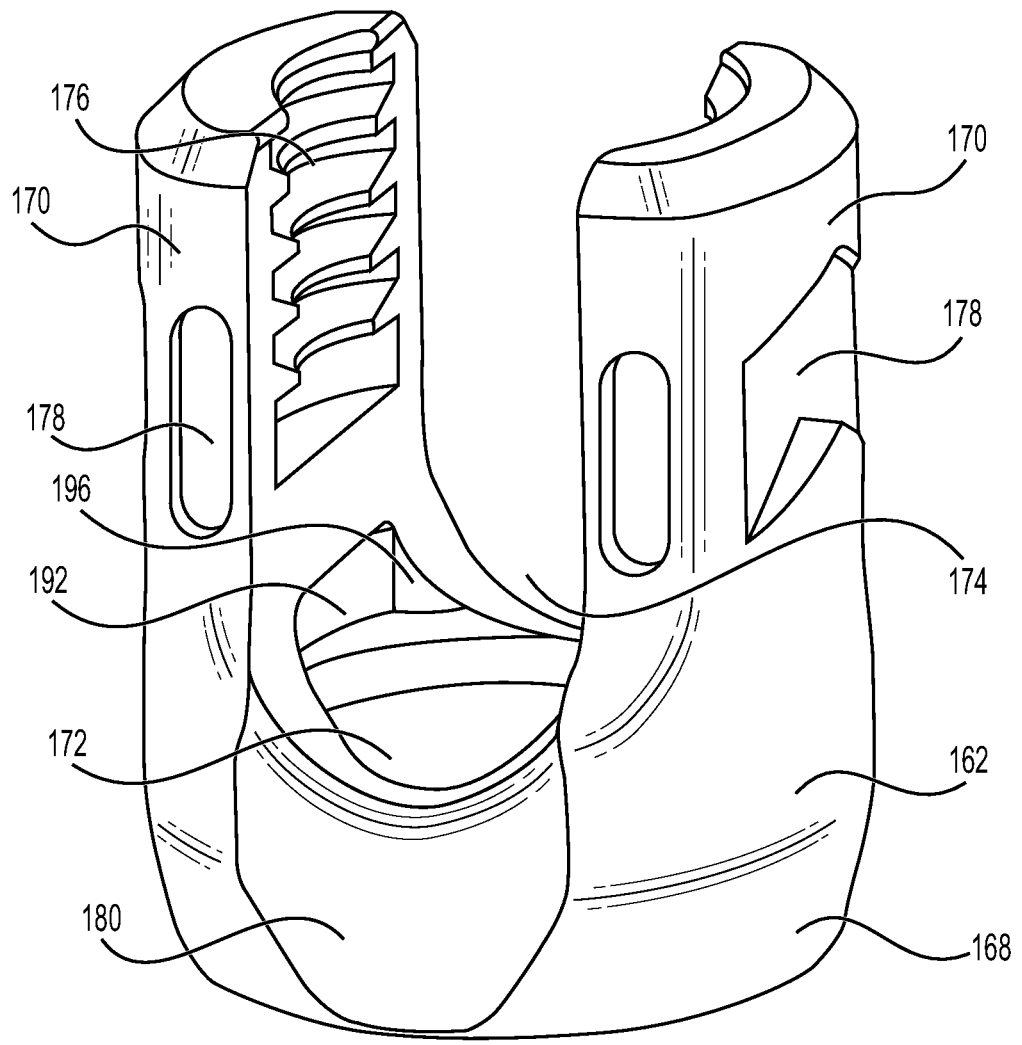
FIG. 23 shows a perspective view of the tulip head according to one embodiment.

The saddle 164 may be rotatable within the tulip head 162 in order to engage the saddle 164 within the internal bore 192. In one embodiment, the outer profile of the saddle 164 and internal bore 192 of the tulip head 162 may be elliptical in shape, for example, to prevent the saddle 164 from rotating out of alignment. As shown in FIG. 20, the saddle 164 may be inserted from the top of the tulip head 162 with the seat 190 offset about 90° out of alignment with the rod slot 174 of the tulip head 162. After downward insertion into the tulip head 162, as shown in FIG. 21, the saddle 164 may be twisted or rotated about 90° into alignment with the internal bore 92 in the tulip head 162. This rotation allows the seat 190 of the saddle 164 to align with the rod slot 174 of the tulip head 162 such that the rod 18 may be positioned between the arms 170 of the tulip head 162 and into contact with the seat 190 of the saddle 164. In this manner, the saddle 164 may be first inserted in a first initial orientation with the seat 190 at a 90° rotated position relative to its final position, and then subsequently rotated 90° to a second final orientation with the seat 190 aligned with the U-shaped rod slot 174 defined between the arms 170 of the tulip head 162.

One or more grooves or engagement recesses 194 may be cut into the saddle 164 to allow for an interface with an assembly tool to facilitate rotation of the saddle 164. For example, a pair of opposed engagement recesses 194 may be provided through the upper surface 182 on opposite sides of the bore 188. The engagement recesses 194 may help to eliminate interference with the tulip 162 when in the up position, and permit engagement with an assembly tool to rotate the saddle 164. A lead 196 in to the ellipse within the tulip 162 may ensure that the saddle 164 is not damaged during rotation.

In one embodiment, the saddle 164 retains a clamp 166 that accepts the spherical screw head 80, thereby permitting polyaxial motion. The clamp 166 may be the same or similar to clamp 156. The clamp 166 may include a body with at least one slit 198 formed therein. The slit 198 may allow for the clamp 166 to constrict and securely engage the head 80 of the bone screw 14. Outer surfaces of the clamp 166 may abut and engage with the saddle 164 and/or tulip body 168. Examples of clamps elements are described in more detail, for example, in U.S. Pat. No. 10,368,917, which is incorporated by reference herein in its entirety for all purposes.

As shown in FIG. 20, when the saddle 164 is in the upward position, the clamp 166 is able to accept the screw head 80. The spherical screw head 80 may be inserted into the bottom of the clamp 166. The clamp 166 may be permitted to expand within the tulip head 162, for example, due to the one or more slits 198 in the clamp 166. As shown in FIG. 21, the saddle 164 is then translated down to close clearance within the tulip head 162, which prevents expansion of the clamp 166 so that the spherical screw head 80 may not be released. The saddle 164 is translated downward to the elliptical bore 192 of the tulip 162. Then, the saddle 164 is rotated perpendicular to the rod slot 174. Thus, the saddle 164 is secured by rotation of the saddle 164, for example, by 90° about the central longitudinal axis A of the implant and into engagement with the elliptical bore 192 within the tulip head 162. Once rotated, the seat 190 of the saddle 164 is properly in alignment with the rod slot 174. The rotatable saddle 164 may allow for ease of assembly and elimination of the complex and tightly toleranced bump. In addition, potential inadvertent release of the saddle 164 to the up position, for example, due to pressing of the saddle past the bump may also be reduced or eliminated.

The devices and assemblies described herein may allow for improved functionality, strength, and/or ease of manufacturing for pedicle screw head assemblies. The component features may simplify geometries to reduce profile, increase strength, and/or simplify manufacturing and assembly.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that all components of the various embodiments disclosed above may be combined or modified in any suitable configuration.

What is claimed is:

1. An orthopedic fixation assembly comprising:
a tulip head having two arms defining a rod slot therebetween, the tulip head having a bore extending therethrough and a groove disposed about the bore;
a bone fastener including a screw head receivable in the tulip head and a shaft configured for engaging bone;
a saddle having an upper surface defining a rod seat, the saddle configured to secure the screw head of the bone fastener, wherein the saddle is insertable into the tulip head in a first position and the saddle is rotatable into a second position; and
a threaded locking cap threadable between the two arms of the tulip head to secure the rod therein
wherein one or more relief cuts in the tulip head lead into the groove to allow rotation of the saddle into alignment in a single direction.

2. The orthopedic fixation assembly of claim 1, wherein the saddle is rotated 90° about a central longitudinal axis of the tulip head from the first position to the second position.

3. The orthopedic fixation assembly of claim 1, wherein an outer surface of the saddle and the groove are elliptically shaped, thereby preventing the saddle from rotating out of alignment.

4. The orthopedic fixation assembly of claim 1, wherein the saddle includes a through bore and a pair of engagement recesses in the upper surface of the saddle on opposite sides of the through bore, wherein the engagement recesses are configured to interface with an assembly tool to facilitate rotation of the saddle.

5. The orthopedic fixation assembly of claim 1, wherein the saddle includes a pair of wings extending outwardly from opposite sides of the saddle, wherein the wings are receivable in the groove in the tulip head.

6. The orthopedic fixation assembly of claim 1, wherein when the locking cap is threaded downwardly onto the rod, the rod pushes against the seat of the saddle, and the saddle secures the bone fastener.

7. The orthopedic fixation assembly of claim 1, wherein the bore of the tulip head defines an internal taper, wherein the screw head is prevented from disengaging from the tulip head by the internal taper.

8. The orthopedic fixation assembly of claim 1, further comprising a clamp for accepting the screw head, wherein when the saddle is in the first position, the clamp is able to accept the screw head, and when the saddle is in the second position, the bone fastener is locked in position.

9. An orthopedic fixation device comprising:
a tulip head having two arms defining a rod slot therebetween, each of the arms defining a threaded portion along an interior surface, the tulip head having a bore extending therethrough and a groove disposed about the bore, wherein the tulip head defines a first indicator;
a locking cap having an outer body defining a thread, wherein the locking cap is threadable between the two arms of the tulip head to secure a rod therein, and wherein the locking cap defines a second indicator to show the best alignment to start threading the locking cap into the tulip head; and
a saddle having an upper surface defining a rod seat, wherein the saddle is insertable into the tulip head in an unlocked position, and the saddle is rotatable into a locked position,
wherein the first indicator is at least one laser mark on an upper surface of one of the arms.

10. The orthopedic fixation device of claim 9, wherein the second indicator is a groove extending radially outward on a top surface of the locking cap.

11. The orthopedic fixation device of claim 10, further comprising a third indicator including a cutout in a side of one of the arms.

12. The orthopedic fixation device of claim 10, wherein the locking cap has a first thread at a bottom of the locking cap, wherein the first thread is broken by a radiused cut, thereby increasing the likelihood of the thread engaging with the threaded portion of the tulip head.

13. The orthopedic fixation device of claim 10, wherein starts of the threads of the locking cap and tulip head are timed when the first and second indicators are aligned, thereby helping to avoid off angle insertion.

14. The orthopedic fixation device of claim 10, wherein the thread of the locking cap includes a top surface angled inward towards a minor diameter and a bottom surface angled outward away from the minor diameter.

* * * * *